United States Patent
Nose et al.

(10) Patent No.: US 8,344,191 B2
(45) Date of Patent: Jan. 1, 2013

(54) PROCESS FOR PREPARING 2,3,3,3-TETRAFLUOROPROPENE

(75) Inventors: Masatoshi Nose, Settsu (JP); Daisuke Karube, Settsu (JP); Akinari Sugiyama, Settsu (JP); Takashi Shibanuma, Settsu (JP); Takehiro Chaki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/056,448

(22) PCT Filed: Jul. 24, 2009

(86) PCT No.: PCT/JP2009/063629
§ 371 (c)(1),
(2), (4) Date: Jan. 28, 2011

(87) PCT Pub. No.: WO2010/013796
PCT Pub. Date: Feb. 4, 2010

(65) Prior Publication Data
US 2011/0178344 A1     Jul. 21, 2011

Related U.S. Application Data

(60) Provisional application No. 61/084,715, filed on Jul. 30, 2008, provisional application No. 61/213,007, filed on Apr. 28, 2009.

(51) Int. Cl.
*C07C 17/00* (2006.01)
(52) U.S. Cl. .......................... 570/165; 570/164
(58) Field of Classification Search .................. 570/164, 570/165
See application file for complete search history.

(56) References Cited

U.S. PATENT DOCUMENTS

| | | | |
|---|---|---|---|
| 2,931,840 | A | 4/1960 | Marquis |
| 2,996,555 | A | 8/1961 | Rausch |
| 3,996,299 | A | 12/1976 | Fozzard |
| 2006/0258891 | A1 | 11/2006 | Mukhopadhyay et al. |
| 2007/0112228 | A1* | 5/2007 | Mukhopadhyay et al. ... 570/161 |
| 2010/0022808 | A1 | 1/2010 | Rao et al. |
| 2010/0210882 | A1 | 8/2010 | Sharratt et al. |

FOREIGN PATENT DOCUMENTS

| | | |
|---|---|---|
| JP | 63-211245 | 9/1988 |
| WO | 2008/030440 | 3/2008 |
| WO | 2008/040969 | 4/2008 |
| WO | 2008/060614 | 5/2008 |

OTHER PUBLICATIONS

International Search Report issued Sep. 23, 2009 in International (PCT) Application No. PCT/JP/2009/063629.
PCT Written Opinion of the International Searching Authority issued Sep. 23, 2009 in International (PCT) Application No. PCT/JP/2009/063629.
George L. Heard et al., "1,2-FCl Rearrangement as an Intermediate Step in the Unimolecular 1,3-HCl Elimination from Chlorofluoropropanes," J. Phys. Chem. A., vol. 105, No. 9, pp. 1622-1625, 2001.
R.N. Haszeldine et al., "Addition of Free Radicals to Unsaturated Systems. Part Direction of Radical Addition to Chloro-1: 1-difluoroethylene," J. Chem. Soc., pp. 2193-2197, 1957.
R.N. Haszeldine et al., "Free-Radical Addition to Unsaturated Systems. Part XVII. Reaction of Trifluoroiodomethane with Mixtures of Ethylene and Vinyl Fluoride and Ethylene and Propene," J. Chem. Soc., vol. 3, pp. 414-421, 1970.
R. Eric Banks et al., "Preparation of 2,3,3,3-tetrafluoropropene from trifluoroacetylacetone and sulphur tetrafluoride," J. Flu. Chem., vol. 82, pp. 171-174, 1997.

* cited by examiner

*Primary Examiner* — Jafar Parsa
(74) *Attorney, Agent, or Firm* — Wenderoth, Lind & Ponack, L.L.P.

(57) ABSTRACT

The present invention provides a process for producing 2,3,3-tetrafluoropropene represented by the formula $CF_3CF{=}CH_2$, comprising contacting a fluorine-containing propane represented by the formula $CF_2XCFYCH_2Z$, wherein X is Cl, Br, or I; one of Y and Z is H, and the other is F, Cl, Br, or I, with at least one catalyst selected from the group consisting of chromium oxides, fluorinated chromium oxides, and iron fluorides in a gas phase. According to the process of the invention, 2,3,3,3-tetrafluoropropene can be easily produced under economically advantageous conditions.

5 Claims, No Drawings

PROCESS FOR PREPARING 2,3,3,3-TETRAFLUOROPROPENE

This application claims priority of U.S. Provisional Application No. 61/084,715 filed Jul. 30, 2008 and U.S. Provisional Application No. 61/213,007 filed Apr. 28, 2009.

TECHNICAL FIELD

The present invention relates to a process for preparing 2,3,3,3-tetrafluoropropene.

BACKGROUND ART 2,3,3,3-Tetrafluoropropene represented by the formula $CF_3CF=CH_2$ (HFO-1234yf) is a compound that is useful as a refrigerant.

Patent Literature (PTL) 1 listed below, for example, dFiscloses a process for preparing HFO-1234yf, wherein a compound represented by $CX_3CF_2CH_3$ (X is a halogen atom) is contacted with hydrogen fluoride in the presence of chromium oxyfluoride at a molar ratio of hydrogen fluoride to the starting material of 2-40 mol to 1 mol. In Patent Literature 1, however, $CCl_3CF_2CH_3$ (HCFC-242cb) is the only compound specifically used as the starting material, in which case hydrogen fluoride is used in large excess, i.e., in an amount of 18 mol per mol of the starting material, resulting in poor efficiency.

Non-Patent Literature (NPL) 1 proposes a reaction route that includes the production of $CF_3CFClCH_3$ (HCFC-244bb) by 1,2-rearrangement of Cl and F in $CF_2ClCF_2CH_3$ (HCFC-244 cc), followed by the elimination of HCl, thereby producing HFO-1234yf. As a result of the test conducted by the present inventors, however, the reaction via this reaction route did not proceed. Therefore, HFO-1234yf cannot be obtained by the process disclosed in Non-Patent Literature 1.

As another preparation process, Non-Patent Literature 2 discloses a single-step process wherein $CF_3CF_2CH_2X$ (X=Cl or I) is reacted with zinc (Zn) in ethanol. This process, however, is not suitable for industrial-scale production, since zinc is expensive, and large amounts of wastes are produced. Patent Literature 2 listed below discloses a process that involves the synthesis of $CF_3CF=CCl_2$ (HFC-1214ya) by dehydrofluorination of $CF_3CF_2CHCl_2$ (HCFC-225ca), and reduction of the HFC-1214ya with hydrogen in a gas phase in the presence of a palladium catalyst supported on a carrier such as alumina, fluorinated alumina, aluminum fluoride, or a mixture thereof, thereby obtaining a mixture containing at least 50% of HFO-1234yf. This process also, however, does not provide a satisfactory yield, and requires further improvement.

Other processes for preparing HFO-1234yf that have been reported include a process wherein chloromethyl tetrafluoropropanoate is reacted with an amine (Patent Literature 3); a process that involves the thermal decomposition of 1-trifluoromethyl-1,2,2-trifluorocyclobutane (Patent Literature 4); a process wherein chlorotrifluoroethylene ($CClF=CF_2$) is reacted with methyl fluoride ($CH_3F$) in the presence of a Lewis acid such as $SbF_5$ (Patent Literature 5); and a process that involves the thermal decomposition of tetrafluoroethylene ($CF_2=CF_2$) and chloromethane ($CH_3Cl$) (Patent Literature 6). Further, Non-Patent Literatures 3 and 4 listed below also disclose processes for preparing HFO-1234yf.

These processes, however, are not considered to be effective for industrial purposes since the starting materials are difficult to produce and are not easily obtained, the reaction conditions are severe, the reaction reagents are expensive, the yield is low, etc. Thus, there is a need for an economically suitable process for easily producing HFO-1234yf.

CITATION LIST

Patent Literature

PTL 1: U.S. Pat. No. 2,996,555
PTL 2: WO 2008/060614 A2
PTL 3: Japanese Unexamined Patent Publication No. 63-211245
PTL 4: U.S. Pat. No. 3,996,299
PTL 5: U.S. Patent Application Publication No. 2006/258891
PTL 6: U.S. Pat. No. 2,931,840

Non Patent Literature

NPL 1: J. Phys. Chem. A. 2001, 105 (9), pp. 1622-1625
NPL 2: J. Chem. Soc., 1957, 2193-2197
NPL 3: J. Chem. Soc., 1970, 3, 414-421
NPL 4: J. Flu. Chem., 1997, 82, 171-174

SUMMARY OF INVENTION

Technical Problem

The present invention was made in view of the above-described prior art problems. A principal object of the invention is to provide a process for easily producing 2,3,3,3-tetrafluoropropene under economically advantageous conditions.

Solution to Problem

The present inventors conducted extensive research to achieve this object. Consequently, the inventors found that, according to a process wherein a specific fluorine-containing propane such as a compound represented by the formula $CF_2ClCF_2CH_3$ (HCFC-244 cc) is used as a starting material, and contacted with a specific catalyst in a gas phase, 2,3,3,3-tetrafluoropropene can be produced directly from the above-mentioned starting material by a single-step reaction procedure, with a good selectivity and a high yield. In particular, the inventors found that when specific amounts of oxygen and hydrogen fluoride (HF) are also present during this reaction, the conversion of the fluorine-containing propane used as a starting material can be significantly improved, and excellent catalytic activity can be maintained over an extended period of time by suppressing the degradation of the catalyst. The present invention was accomplished as a result of further research based on these findings.

The present invention provides a process for preparing 2,3,3,3-tetrafluoropropene as summarized below.

1. A process for producing 2,3,3,3-tetrafluoropropene represented by the formula $CF_3CF=CH_2$, comprising contacting a fluorine-containing propane represented by the formula $CF_2XCFYCH_2Z$, wherein X is Cl, Br, or I; one of Y and Z is H, and the other is F, Cl, Br, or I, with at least one catalyst selected from the group consisting of chromium oxides, fluorinated chromium oxides, and iron fluorides in a gas phase.

2. The process according to item 1, wherein the fluorine-containing propane represented by the formula $CF_2XCFYCH_2Z$ is a compound wherein one of Y and Z is H, and the other is F.

3. The process according to item 2, wherein the fluorine-containing propane represented by the formula $CF_2XCFYCH_2Z$ is a compound represented by the formula $CF_2ClCF_2CH_3$.

4. The process according to any one of items 1 to 3, wherein the reaction is carried out in the presence of not more than 2 mol of hydrogen fluoride per 1 mol of the fluorine-containing propane represented by the formula $CF_2XCFYCH_2Z$.

5. The process according to any one of items 1 to 4, wherein the reaction is carried out in the presence of oxygen.

6. The process according to any one of items 1 to 5, wherein the reaction is carried out in the presence of hydrogen fluoride and oxygen, the amount of the hydrogen fluoride being from 0.1 to 2 mol per mol of the fluorine-containing propane represented by the formula $CF_2XCFYCH_2Z$, and the amount of the oxygen being from 0.1 to 21 mol % based on the total amount of the fluorine-containing propane, hydrogen fluoride, and oxygen.

7. The process according to any one of items 1 to 6, wherein the catalyst is a chromium oxide represented by the formula $CrO_m$, wherein $1.5<m<3$, or a fluorinated chromium oxide obtained by fluorinating the chromium oxide.

In the invention, a fluorine-containing propane represented by the formula $CF_2XCFYCH_2Z$, wherein X is Cl, Br, or I; one of Y and Z is H, and the other is F, Cl, Br, or I, is used as a starting material.

Preferable among these fluorine-containing propanes represented by the formula above are compounds wherein one of Y and Z is H, and the other is F, because the reaction proceeds efficiently. Particularly preferable is a compound wherein $X=Cl, Y=F$, and $Z=H$, i.e., a compound represented by the formula $CF_2ClCF_2CH_3$ (HCFC-244 cc). HCFC-244 cc is a known compound and obtainable by, for example, a process wherein $CF_2ClCF_2CHCl_2$ (HCFC-224ca) is reduced (see Japanese Unexamined Patent Publication No. 2-131437), a process wherein $CCl_3CF_2CH_3$ (HCFC-242cb) is fluorinated (see Japanese Unexamined Patent Publication No. 2-17138), or a process wherein $CCl_3CCl_2CH_3$ (CFC-240ab), $CCl_3CFClCH_3$ (HCFC-241bb), or the like is fluorinated (see Japanese Unexamined Patent. Publication No. 2-204437).

The present invention requires using the above-mentioned fluorine-containing propane represented by the formula $CF_2XCFYCH_2Z$ as a starting material, and contacting this starting material with at least one catalyst selected from the group consisting of chromium oxides, fluorinated chromium oxides, and iron fluorides in a gas phase. According to this process, by employing the reaction conditions described below, the desired 2,3,3,3-tetrafluoropropene (HFO-1234yf) represented by the formula $CF_3CF=CH_2$ can be obtained by a single-step reaction procedure, with a good selectivity and a high yield.

Among the catalysts used in the invention, usable as chromium oxides are, for example, those of the formula $CrO_m$, wherein m is $1.5<m<3$, preferably $2<m<2.75$, and more preferably $2<m<2.3$. One example of a method for preparing such a chromium oxide is as follows.

First, an aqueous solution of a chromium salt (chromium nitrate, chromium chloride, chromium alum, chromium sulfate, or the like) is mixed with aqueous ammonia to produce a precipitate of chromium hydroxide. The precipitate is then filtered, washed, and dried. Drying may be performed, for example, in air at about 70 to about 200° C., and particularly at about 120° C., for about 1 to about 100 hours, and particularly for about 12 hours. The product obtained at this stage is referred to as being in the state of chromium hydroxide.

This product is subsequently disintegrated into a powder. The disintegrated chromium hydroxide powder is blended with graphite in an amount of about 3 wt % or less, as needed, and formed into pellets using a tableting machine. The pellets may, for example, be about 3.0 mm in diameter and about 3.0 mm in height.

Lastly, the molded pellets are calcined in an inert atmosphere, e.g., in a nitrogen stream, to produce an amorphous chromium oxide.

The calcined chromium oxide has a specific surface area of about 170 $m^2/g$ or more, preferably about 180 $m^2/g$ or more, and more preferably about 200 $m^2/g$ or more. The upper limit of the specific surface area is about 240 $m^2/g$, and preferably about 220 $m^2/g$. A specific surface area of 240 $m^2/g$ or more increases the activity, but also increases the degradation rate, whereas a specific surface area of less than 170 $m^2/g$ reduces the catalytic activity; thus, these ranges are undesired. Note that the specific surface area is herein measured according to the BET method.

A fluorinated chromium oxide can be prepared according to the method described in Japanese Unexamined Patent Publication No. 5-146680. A fluorinated chromium oxide can be obtained by, for example, fluorinating the chromium oxide obtained by the above-described method with hydrogen fluoride (HF treatment). The pressure during fluorination is not limited, but is preferably a pressure at which the catalytic reaction is performed. The fluorination temperature is from about 100 to about 460° C.

The fluorination treatment reduces the surface area of the catalyst; in general, however, the higher the specific surface area is, the higher the activity is. Thus, the specific surface area of the fluorinated chromium oxide is preferably from about 25 to about 130 $m^2/g$, and more preferably from about 40 to about 100 $m^2/g$, but is not limited to this range.

The fluorination reaction of the chromium oxide may be performed, prior to carrying out the process of the invention described below, by supplying hydrogen fluoride to a reactor charged with the chromium oxide.

Although the degree of fluorination is not limited, a fluorinated chromium oxide having a fluorine content of about 10 to about 30 wt % can be suitably used.

Further, the chromium-based catalyst disclosed in Japanese Unexamined Patent Publication No. 11-171806 is usable as a chromium oxide catalyst or a fluorinated chromium oxide catalyst in the invention. This chromium-based catalyst principally comprises a chromium compound containing at least one metal element selected from the group consisting of indium, gallium, cobalt, nickel, zinc, and aluminum, wherein the average valence of the chromium in the chromium compound is +3.5 or more and +5.0 or less, and the chromium-based catalyst is amorphous.

The type of the iron fluoride used as a catalyst is not limited, but is preferably an iron fluoride represented by the formula $FeF_x$, wherein x is from 2 to 3. Examples of such iron fluorides that can be used include commercially available products in the form of pellets, pellets produced from commercially available powdery products using a compacting machine or the like, etc.

The at least one catalyst selected from the group consisting of chromium oxides, fluorinated chromium oxides, and iron fluorides can be supported on a carrier such as alumina, activated carbon, or the like.

In the process of the invention for preparing 2,3,3,3-tetrafluoropropene (HFO-1234yf), the reaction may be typically performed by supplying the fluorine-containing propane represented by the formula $CF_2XCFYCH_2Z$, wherein X, Y, and Z are as defined above, into a reactor charged with the above-mentioned catalyst in a gas phase. This reaction method is assumed to involve the formation of a fluorine-containing propene represented by the formula $CF_2XCF=CH_2$ by the elimination of the hydrogen halide represented by YZ from the fluorine-containing propane represented by the formula $CF_2XCFYCH_2Z$ used as a starting material; and the reaction of the fluorine-containing propene with the eliminated hydrogen fluoride to rapidly fluorinate the halogen atom at the allylic position of the fluorine-containing propene represented by the formula $CF_2XCF=CH_2$, resulting in the production of desired 2,3,3,3-tetrafluoropropene (HFO-1234yf) represented by the chemical formula $CF_3CF=CH_2$.

In this case, when the eliminated hydrogen halide (YZ) is HF, i.e., when one of Y and Z is H, and the other is F in the fluorine-containing propane represented by the formula $CF_2XCFYCH_2Z$, the reaction can proceed without the addition of hydrogen fluoride (HF), resulting in an excellent HF utilization efficiency.

The above-mentioned reaction mechanism is specific to the fluorine-containing propane represented by the formula $CF_2XCFYCH_2Z$, and essentially differs from that of the fluorination reaction of HCFC-242cb disclosed in PTL 1.

Thus, in the invention, the fluorine-containing propane wherein one of Y and Z is H and the other is F can be used alone as a starting material; however, hydrogen fluoride may be additionally supplied. When hydrogen fluoride is supplied, the conversion of the starting material may decrease to some extent, but the selectivity to $CF_3CF=CH_2$ (HFO-1234yf) can be improved.

When a compound of the formula $CF_2XCFYCH_2Z$ wherein neither Y nor Z is F is used, hydrogen fluoride must be added.

When hydrogen fluoride is used, in general, it may be supplied into a reactor together with the fluorine-containing propane represented by the formula $CF_2XCFYCH_2Z$, in a gas phase. In general, the amount of hydrogen fluoride is preferably from about 2 mol or less, and more preferably from about 1.5 mol or less, based on 1 mol of the fluorine-containing propane represented by the formula $CF_2XCFYCH_2Z$.

An amount of hydrogen fluoride exceeding 2 mol based on 1 mol of the fluorine-containing propane represented by the formula $CF_2XCFYCH_2Z$ is undesirable because the selectivity to HFO-1234yf will not be significantly improved, and the conversion of the fluorine-containing propane may decrease.

If the amount of hydrogen fluoride is small, the amount of HCFO-1233yf produced may increase, or the catalyst may degrade. It is thus preferred that 0.1 mol or more of hydrogen fluoride be used based on 1 mol of the fluorine-containing propane represented by the formula $CF_2XCFYCH_2Z$.

Therefore, when the amount of hydrogen fluoride is from 0.1 to 2 mol based on 1 mol of the fluorine-containing propane represented by the formula $CF_2XCFYCH_2Z$, both of the conversion of the fluorine-containing propane used as a starting material and the selectivity to HFO-1234yf can be maintained within a satisfactory range.

The starting material may be supplied as is into the reactor, or may be diluted with an inert gas such as nitrogen, helium, or argon.

The starting material may also be supplied to the reactor together with oxygen, in order to maintain the catalytic activity for an extended period of time. In this case, the amount of oxygen is preferably from about 0.1 mol % or more, and more preferably from about 0.1 to about 21 mol %, based on the total amount of the fluorine-containing propane represented by the formula $CF_2XCFYCH_2Z$, hydrogen fluoride, and oxygen. If the amount of oxygen is too small, the effect obtained by the addition of oxygen will be low, whereas if the amount of oxygen is too large, the oxygen will be wastefully used, and the production rate of HFO-1234yf per unit amount of catalyst will decrease, which is undesirable.

In the invention, particularly when hydrogen fluoride is supplied in an amount of about 0.1 mol or more, and preferably about 0.1 to about 2 mol, based on 1 mol of the fluorine-containing propane represented by the formula $CF_2XCFYCH_2Z$, and oxygen is supplied in an amount of about 0.1 to about 21 mol %, and preferably about 5 to about 21 mol %, based on the total number of moles of the fluorine-containing propane, hydrogen fluoride, and oxygen supplied, the conversion of the fluorine-containing propane used as a starting material can be significantly improved, and excellent catalytic activity can be maintained for an extended period of time by suppressing the degradation of the catalyst.

The type of the reactor used in the process of the invention is not limited; examples of usable reactors include an adiabatic reactor charged with the catalyst, a multitube reactor heated with a heating medium, etc. The reactor used is preferably made of a material resistant to the corrosive action of hydrogen fluoride, such as Hastelloy, Inconel, Monel, or the like.

In the process of the invention, the reaction temperature in the reactor is preferably from about 200 to about 450° C., and more preferably from about 250 to about 400° C. If the temperature is higher than this range, the catalytic activity will decrease, whereas if the temperature is lower, the conversion of the starting material will become low, which is undesirable.

The reaction can be performed at any pressure, e.g., at ordinary pressure or under increased pressure. More specifically, the reaction of the invention can be performed at atmospheric pressure (0.1 MPa), but may be performed at an increased pressure of up to about 1.0 MPa.

Although the reaction time is not limited, the contact time represented by the ratio of the catalyst weight W (g) relative to the total flow rate $F_0$ (flow rate at 0° C. and 1 atm: cc/sec) of the starting gases (i.e., the fluorine-containing propane, hydrogen fluoride, and oxygen) passed in the reaction system, i.e., $W/F_0$, is from 5 to 100 g·sec/cc, and preferably from about 10 to about 40 g·sec/cc.

A reaction product containing $CF_3CF=CH_2$ (HFO-1234yf) can be obtained at the outlet of the reactor.

The reaction product can be purified by distillation or the like and collected. Unreacted starting materials can be separated and purified, and then returned into the reactor and recycled. Because unreacted starting materials can be thus recycled, high productivity can be maintained even if the conversion of the starting material is low.

Advantageous Effects of Invention

According to the process of the invention, $CF_3CF=CH_2$ (HFO-1234yf) can be directly produced from the fluorine-containing propane represented by the formula $CF_2XCFYCH_2Z$ by the single-step reaction.

In particular, when specific amounts of oxygen and hydrogen fluoride are also present in the reaction system, the conversion of the fluorine-containing propane used as a starting material can be significantly improved, and excellent catalytic activity can be maintained for an extended period of time by suppressing the degradation of the catalyst.

Accordingly, the process of the invention can be an industrially advantageous process for preparing $CF_3CF=CH_2$ (HFO-1234yf).

DESCRIPTION OF EMBODIMENTS

The present invention is described in greater detail below, using Production Examples of $CF_2ClCF_2CH_3$ (HCFC-244cc) that can be suitably used among the starting materials, and Examples of the invention.

Production Example 1

Synthesis of $CF_2ClCF_2CH_3$ (HCFC-244 cc)

A 3 L stainless-steel autoclave was charged with 330 g of $CF_2ClCF_2CHCl_2$ (HCFC-224ca) (1.5 mol), 1500 ml of ethanol, 291 g of sodium acetate (3546 mmol), and 15 g of a catalyst containing palladium supported on activated carbon (the amount of palladium: 10 wt %), and sealed.

The autoclave was purged with hydrogen gas, and hydrogen gas was supplied thereto so that the internal pressure was 1 MPa at room temperature, and then the contents were stirred. When the hydrogen gas was consumed to cause the internal pressure to drop, additional hydrogen gas was supplied, as needed, to maintain the internal pressure at 1 MPa. Once the drop of the internal pressure had stopped, the autoclave was heated to 65° C. Stirring was continued for 10 hours while heating the autoclave with the internal pressure maintained at a minimum of 1 MPa.

After cooling to room temperature, the hydrogen gas was removed, and the solution in the autoclave was analyzed by gas chromatography. As a result, the conversion of $CF_2ClCF_2CHCl_2$ (HCFC-224ca) was 100%; and $CF_2ClCF_2CH_3$ (HCFC-244 cc) and $CF_2ClCF_2CH_2Cl$ (HCFC-234cb) were produced at a molar ratio of 60:32. Separation was subsequently performed at ordinary pressure, using a rectification column with a theoretical plate number of 10; as a result, 98.6 g of $CF_2ClCF_2CH_3$ (HCFC-244 cc) was obtained. The purity of the resulting HCFC-244 cc was found to be 99.0% by the quantification using gas chromatography.

Example 1

A tubular Hastelloy reactor with an inner diameter of 15 mm and a length of 1 m was charged with 30 g of a catalyst obtained by fluorinating a chromium oxide represented by the formula $CrO_2$ (fluorine content: about 15 wt %). The reactor was maintained at atmospheric pressure (1 atm) and 300° C., and anhydrous hydrogen fluoride (HF) gas was supplied to the reactor at 60 cc/min (flow rate at 0° C. and 1 atm) for 1 hour. $CF_2ClCF_2CH_3$ (HCFC-244 cc) gas was subsequently supplied at a rate of 30 cc/min (flow rate at 0° C. and 1 atm), and the temperature of the reactor was changed to 320° C. The molar ratio of HF to HCFC-244 cc was 2, and the contact time $(W/F_o)$ was 20 g·sec/cc. One hour after the desired reaction temperature was reached, the outlet gas from the reactor was analyzed using gas chromatography. The results are shown in Table 1.

The structure of each product was as follows:
$CF_3CF=CH_2$ (HFO-1234yf)
$CF_3CF_2CH_3$ (HFC-245cb)
$CF_2ClCF=CH_2$ (HCFO-1233yf)
$CF_3CCl=CH_2$ (HCFO-1233xf)

Example 2

The experiment was conducted under the same conditions as Example 1, except that the amount of the catalyst was changed to 25 g, and the flow rate of the anhydrous hydrogen fluoride (HF) gas was changed to 45 cc/min (flow rate at 0° C. and 1 atm). The molar ratio of HF to HCFC-244 cc was 1.5, and the contact time $(W/F_o)$ was 20 g·sec/cc. The analytical results are shown in Table 1.

Example 3

The experiment was conducted under the same conditions as Example 1, except that the amount of the catalyst was changed to 20 g, and the flow rate of the anhydrous hydrogen fluoride (HF) gas was changed to 30 cc/min (flow rate at 0° C. and 1 atm). The molar ratio of HF to HCFC-244 cc was 1, and the contact time $(W/F_o)$ was 20 g·sec/cc. The analytical results are shown in Table 1.

Example 4

The experiment was conducted under the same conditions as Example 3, except that the reaction temperature was changed to 280° C. The molar ratio of HF to HCFC-244 cc was 1, and the contact time $(W/F_o)$ was 20 g·sec/cc. The analytical results are shown in Table 1.

Example 5

The experiment was conducted under the same conditions as Example 1, except that the amount of the catalyst was changed to 15 g, and the flow rate of the anhydrous hydrogen fluoride (HF) gas was changed to 15 cc/min (flow rate at 0° C. and 1 atm). The molar ratio of HF to HCFC-244 cc was 0.5, and the contact time $(W/F_0)$ was 20 g·sec/cc. The analytical results are shown in Table 1.

Example 6

A tubular Hastelloy reactor with an inner diameter of 15 mm and a length of 1 m was charged with 20 g of the same catalyst as that used in Example 1 (fluorine content: about 15 wt %). The reactor was maintained at atmospheric pressure (1 atm) and 300° C., and anhydrous hydrogen fluoride (HF) gas was supplied to the reactor at 60 cc/min (flow rate at 0° C. and 1 atm) for 1 hour. The supply of HF was subsequently ceased, and each of nitrogen ($N_2$) gas and $CF_2ClCF_2CH_3$ (HCFC-244 cc) gas was supplied at 30 cc/min (flow rate at 0° C. and 1 atm), and the temperature of the reactor was changed to 350° C. The molar ratio of HF to HCFC-244 cc was 0, and the contact time $(W/F_o)$ was 20 g·sec/cc. One hour after the desired reaction temperature was reached, the outlet gas from the reactor was analyzed using gas chromatography. The results are shown in Table 1.

Example 7

A tubular Hastelloy reactor with an inner diameter of 15 mm and a length of 1 m was charged with 16 g of the same catalyst as that used in Example 1 (fluorine content: about 15 wt %). The reactor was maintained at atmospheric pressure (1 atm) and 300° C., and anhydrous hydrogen fluoride (HF) gas was supplied to the reactor at 60 cc/min (flow rate at 0° C. and 1 atm) for 1 hour. The supply of HF was subsequently ceased, and nitrogen ($N_2$) gas was supplied at a rate of 60 cc/min (flow rate at 0° C. and 1 atm) for another 1 hour. The supply of nitrogen ($N_2$) gas was subsequently ceased, and $CF_2ClCF_2CH_3$ (HCFC-244 cc) gas was supplied at a rate of 48 cc/min (flow rate at 0° C. and 1 atm), and the temperature of the reactor was changed to 350° C. The molar ratio of HF to HCFC-244 cc was 0, and the contact time $(W/F_o)$ was 20 g·sec/cc. One hour after the desired reaction temperature was reached, the outlet gas from the reactor was analyzed using gas chromatography. The results are shown in Table 2.

Example 8

A tubular Hastelloy straight reactor (diameter: 2.54 cm) equipped with an electric furnace was charged with 82 g of the same fluorinated chromium oxide catalyst as that of Example 1. The reactor was heated to 400° C. while passing nitrogen ($N_2$) gas to dry the catalyst, and the temperature was held at 400° C. for 1 hour. The supply of the nitrogen gas was ceased, and oxygen ($O_2$) gas was introduced at a flow rate of 2.2 cc/min (8 vol % of the total gas flow rate) and $CF_2ClCF_2CH_3$ (HCFC-244 cc) gas was introduced at a flow rate of 25 cc/min via the reactor inlet.

After the elapse of 1 hour from the beginning of the introduction of HCFC-244 cc, the gas flowing from the reactor outlet was analyzed by gas chromatography. The results are shown in Table 2.

Example 9

A tubular Hastelloy straight reactor (diameter: 2.54 cm) equipped with an electric furnace was charged with 8.2 g of the same fluorinated chromium oxide catalyst as that of Example 1. The reactor was heated to 400° C. while passing nitrogen ($N_2$) gas to dry the catalyst, and the temperature was held at 400° C. for 1 hour. The supply of the nitrogen gas was ceased, and anhydrous hydrogen fluoride (HF) gas was introduced at a flow rate of 15 cc/min (0.5 mol per mol of 244 cc), oxygen ($O_2$) gas was introduced at 3.9 cc/min (8 vol % of the total gas flow rate), and $CF_2ClCF_2CH_3$ (HCFC-244 cc) gas was introduced at 30 cc/min via the reactor inlet.

After the elapse of 4 hours from the beginning of the introduction of 244 cc, the gas flowing from the reactor outlet was analyzed by gas chromatography. The results are shown in the column "Ex. 9-1" of Table 2. Additionally, after the elapse of 10 hours from the beginning of the introduction of HCFC-244 cc, the gas at the reactor outlet was analyzed in the same manner as above. As a result, the gas composition was as shown in the column "Ex. 9-2" of Table 2, and no decrease in conversion due to the degradation of the catalyst was observed.

Example 10

A commercially available iron fluoride powder represented by the formula $FeF_2$ was formed into cylindrical pellets with a diameter of about 2 mm and a height of about 5 mm, using a compacting machine. A tubular Hastelloy straight reactor with a diameter of 2.54 cm was charged with 10 g of the iron fluoride catalyst pellets to prepare a reactor. The reactor was heated to 400° C. while passing nitrogen ($N_2$) gas to dry the catalyst, and the temperature was held at 400° C. The supply of the nitrogen gas was subsequently ceased, and a mixed gas of 18 cc/min $CF_2ClCF_2CH_3$ (HCFC-244 cc) gas and 1.6 cc/min oxygen was introduced via the reactor inlet.

After 1 hour from the beginning of the introduction, the gas flowing from the reactor outlet was analyzed by gas chromatography. The analysis revealed that the reaction proceeded at a 244 cc conversion of 1.8%, and HFO-1234yf was obtained in the resulting product at 93% selectivity.

Comparative Example 1

The experiment was conducted under the same conditions as Example 1, except that the amount of the catalyst was changed to 50 g, and the flow rate of the anhydrous hydrogen fluoride (HF) gas was changed to 120 cc/min (flow rate at 0° C. and 1 atm). The molar ratio of HF to HCFC-244 cc was 4.0, and the contact time ($W/F_0$) was 20 g·sec/cc. The analytical results are shown in Table 2.

TABLE 1

| | Ex. 1 | Ex. 2 | Ex. 3 | Ex. 4 | Ex. 5 | Ex. 6 |
|---|---|---|---|---|---|---|
| Reaction Temperature (° C.) | 320 | 320 | 320 | 280 | 320 | 350 |
| HF/HCFC-244 cc (Molar Ratio) | 2.0 | 1.5 | 1.0 | 1.0 | 0.5 | 0 |
| Oxygen Gas/Total Gas (Molar Ratio) | 0 | 0 | 0 | 0 | 0 | 0 |
| HCFC-244 cc Conversion (%) | 10.8 | 14.7 | 16.8 | 14.1 | 17.8 | 19.3 |
| Product Selectivity (%) | | | | | | |
| HFO-1234yf | 94.6 | 92.9 | 84.9 | 88.7 | 82.3 | 72.5 |
| HFC-245cb | 0.5 | 0.2 | 0.3 | 0.1 | 0.3 | 0 |
| HCFO-1233yf | 4.6 | 6.5 | 14.2 | 10.8 | 16.6 | 25.5 |
| HCFO-1233xf | | | | | 0.1 | 0.2 |
| Others | 0.3 | 0.4 | 0.6 | 0.4 | 0.7 | 1.8 |

TABLE 2

| | Ex. 7 | Ex. 8 | Ex. 9-1 | Ex. 9-2 | Comp. Ex. 1 |
|---|---|---|---|---|---|
| Reaction Temperature (° C.) | 350 | 400 | 400 | 400 | 320 |
| HF/HCFC-244 cc (Molar Ratio) | 0 | 0 | 0.5 | 0.5 | 4.0 |
| Oxygen Gas/Total Gas (Molar Ratio) | 0 | 0.08 | 0.08 | 0.08 | 0 |
| HCFC-244 cc Conversion (%) | 24.4 | 50.9 | 40.0 | 45.4 | 4.2 |
| Product Selectivity (%) | | | | | |
| HFO-1234yf | 63.7 | 85.5 | 91.2 | 92.0 | 94.7 |
| HFC-245cb | 0 | 1.8 | 2.3 | 2.1 | 2.0 |
| HCFO-1233yf | 31.4 | 7.1 | 5.6 | 5.7 | 3.1 |
| HCFO-1233xf | 1.8 | | | | |
| Others | 3.1 | 5.6 | 0.9 | 0.2 | 0.2 |

The invention claimed is:

1. A process for producing 2,3,3,3-tetrafluoropropene represented by the formula $CF_3CF=CH_2$, comprising contacting a fluorine-containing propane represented by the formula $CF_2XCFYCH_2Z$, wherein X is Cl, Br, or I; one of Y and Z is H, and the other is F, with at least one catalyst selected from the group consisting of chromium oxides, fluorinated chromium oxides, and iron fluorides in a gas phase in the absence of hydrogen fluoride or in the presence of not more than 2 mol of hydrogen fluoride per 1 mol of the fluorine-containing propane represented by the formula $CF_2XCFYCH_2Z$.

2. The process according to claim 1, wherein the fluorine-containing propane represented by the formula $CF_2XCFYCH_2Z$ is a compound represented by the formula $CF_2ClCF_2CH_3$.

3. The process according to claim 1, wherein the reaction is carried out in the presence of oxygen.

4. The process according to claim 1, wherein the reaction is carried out in the presence of hydrogen fluoride and oxygen, the amount of the hydrogen fluoride being from 0.1 to 2 mol per mol of the fluorine-containing propane represented by the formula $CF_2XCFYCH_2Z$, and the amount of the oxygen being from 0.1 to 21 mol % based on the total amount of the fluorine-containing propane, hydrogen fluoride, and oxygen.

5. The process according to claim 1, wherein the catalyst is a chromium oxide represented by the formula $CrO_m$, wherein $1.5<m<3$, or a fluorinated chromium oxide obtained by fluorinating the chromium oxide.

* * * * *